United States Patent
Cloonan

(10) Patent No.: US 6,602,490 B1
(45) Date of Patent: Aug. 5, 2003

(54) DENTAL CLEANING FORMULATION AND MANUFACTURING PROCESS

(76) Inventor: Richard A. Cloonan, 719 Townsite Dr., Vista, CA (US) 92084

( * ) Notice: Subject to any disclaimer, the term of this patent is extended or adjusted under 35 U.S.C. 154(b) by 0 days.

(21) Appl. No.: 10/086,797

(22) Filed: Mar. 4, 2002

(51) Int. Cl.[7] .............................. A61K 7/16; A61K 7/18
(52) U.S. Cl. .......................................... 424/49; 424/52
(58) Field of Search ..................... 424/49–58

(56) References Cited

U.S. PATENT DOCUMENTS

| | | | |
|---|---|---|---|
| 4,406,882 A | * 9/1983 | Turner et al. | 424/49 |
| 4,548,950 A | * 10/1985 | Baxendale et al. | 514/510 |
| 4,980,152 A | * 12/1990 | Frazier et al. | 424/52 |
| 5,256,402 A | * 10/1993 | Prencipe et al. | 424/53 |
| 5,272,137 A | * 12/1993 | Blase et al. | 514/54 |
| 5,409,907 A | * 4/1995 | Blase et al. | 514/54 |
| 5,658,919 A | * 8/1997 | Ratnaraj et al. | 514/269 |
| 5,759,579 A | * 6/1998 | Singh et al. | 424/485 |
| 6,042,812 A | * 3/2000 | Sanker et al. | 424/49 |
| 6,224,376 B1 | 5/2001 | Cloonan et al. | |
| 6,419,905 B1 | * 7/2002 | Alvarez-Hernandez | 424/49 |
| 6,509,028 B2 | * 1/2003 | Williams et al. | 424/434 |
| 6,511,654 B2 | * 1/2003 | Ibsen et al. | 424/49 |

OTHER PUBLICATIONS

A.E. Winston; S.N. Bhaskar: Caries Prevention in the 21st Century JADA VO. 129, Nov. 1998, PP 1579–1587.

* cited by examiner

*Primary Examiner*—Shep K. Rose
(74) *Attorney, Agent, or Firm*—Henry J. A. Charmasson; John D. Buchaca

(57) ABSTRACT

A dental hygiene preparation of very low toxicity, but with good remineralization properties and effectiveness in removing food particles and plaques from the tooth surfaces is particularly indicated for use by elderly patients and those with compromised immune systems. The preparation uses a nonfermentable sweetener in lieu of Sodium Fluoride, Sodium Monofluorophasphate or Stannous Fluoride as a caries-preventive agent in combination with Potassium Citrate and Disodium Edetate.

21 Claims, No Drawings

DENTAL CLEANING FORMULATION AND MANUFACTURING PROCESS

FIELD OF THE INVENTION

This invention relates to personal hygiene preparations and more particularly to dentifrices, mouth washes and other dental hygiene products.

BACKGROUND OF THE INVENTION

Despite the emphasis on preventive dentistry and the introduction of dentifrices and mouth washes having remineralization properties, tooth decay still affects a Winston and Sindy N. Bhaskar Caries Prevention in the 21st Century Journal of the American Dental Association, VOL. 129., November 1998.

Plaque acids demineralize the teeth and lead to tooth decay. The process usually starts within a few minutes after the ingestion of refined sugar. Caries-preventive treatments rely on the fluoridation of Municipal water supplies and the use of fluoride-containing toothpastes and mouth washes. Fluoride's ability to remineralize enamel is Since the concentration of Calcium ions is low in healthy people, the rate of remineralization is usually slow. High levels of fluoride in toothpaste, prescription mouthwashes and prescription gels are not without risks. Naturally occurring fluoride levels of 10 to 12 parts per million in water found in certain areas of Texas and new Mexico have been blamed for the mottling of tooth enamel and for high incidence of osteosclerosis. The toxicity of of fluoride creates serious risks for the safety of small children and disabled individuals who occasionally swallow tooth paste while brushing teeth. Indeed, containers of most popular brands of toothpaste carry warning legends urging customers to seek professional help or contact a poison control center immediately upon accidental ingestion of more toothpaste than is used for brushing.

Patients with compromised immune systems, such as those suffering from Acquired Immune Deficiency (AIDS) or those undergoing chemotherapeutic treatments are particularly suspectible to mouth ulcers and irritations. Such persons are in great need of a dental preparation that can be used to thoroughly rinse their teeth and mouth, stimulate healing of lesions, and be devoid of any poisoning risks.

SUMMARY OF THE INVENTION

The principal and secondary objects of the inventions are to provide a dental hygiene preparation that can effectively remove plaque and food debris from teeth, braces and prosthetic devices, remineralize tooth enamel over long periods between meals and avoid the toxicity of fluoridation compounds so that it can be effectively used by elderly or handicapped persons as well as those persons affected by mouth ulcers and irritations.

These and other valuable objects are achieved by the preparation that uses in solution, a sequestrant such as Potassium Citrate, a chelating agent such as Dissodium Edetate and a nonfermentable sweetener such as Xylitol in combination with an emulsifying, wetting and solubizing agent such as Polysorbate. The preparation also contains Calcium Ascorbate as antioxidant as well as flavoring agents such as Spearmint and Peppermint. The preparation does not contain any effective amount of Sodium Fluoride, Sodium monoflurophosphate, Stanous Fluoride or any other source of Fluoride.

DESCRIPTION OF THE PREFERRED EMBODIMENT OF THE INVENTION

The dental hygiene preparation according to the invention includes a sequestran such as Sodium Tripolyphospate, Sorbitol, Sodium Citrate and, preferably, Potassium Citrate in a proportion of approximately 0.0013 to 0.032 percent per weight;

a saturated solution of Disodium Edetate in proportion of approximately 0.0003 to 0.04 percent per volume;

Xylitol in a proportion of approximately 0.008 to 0.08 percent per weight;

one or more emulsifying, wetting and solubizing agent such as Polysorbate in a proportion of approximately 0.0132 to 0.32 percent per volume, and Poloxamer in a proportion of 0.0013 to 0.0317 percent per weight; and an antioxidant, preferably Calcium Ascorbate Dihydrate in a proportion of approximately 0.003 to 0.02 percent per weight.

The preparation also, preferably, includes an additional sweetener such as Aspartane and Sodium Saccharin Dihydrate in a proportion of approximately 0.026 to 0.66 percent per weight, as well as some flavoring agent such as Spearmint and Peppermint. Natural glycerin is preferably added as a humectant, plasticizer and tonicity agent. A small amount of alcohol and a coloring agent may also be included.

The preparation does not contain any effective amount of Fluoride compound that could provide free Fluoride as a caries-preventive agent.

The composition of a preferred example of the dental hygiene preparation is provided in Table 1.

TABLE 1

| | |
|---|---|
| Water (purified) | 3.785 l (one gallon) |
| Ethanol 200 Proof U.S.P./N.F. | 15 ml |
| Rectified F.C.C. Oil of Spearmint | 2 ml |
| Natural F.C.C. Oil of Peppermint | 2 ml |
| DL-Menthol Crystal U.S.P./N.F. (Crystals are Mixed into the alcohol solution). | 400 mg |
| Calcium Ascorbate Dihydrate F.C.C. (Powder is mixed into the water). | 400 mg |
| Potassium Citrate F.C.C. (Granules are mixed into water). | 400 mg |
| Polysorbate 20 U.S.P./N.F. | 3 ml |
| Poloxamer 338 U.S.P./N.F. | 400 mg |
| Natural Glycerin U.S./N.F. | 6 ml |
| Xylitol F.C.C. | 1.33 g |
| Disodium Edetate U.S.P./N.F. (100 mg of this powder is mixed in 10 ml of warm purified water to obtain a saturated solution and 1.25 ml of this saturated solution is mixed into the main solution of other ingredients). | 1.25 ml |
| Aspartane (Nutrasweet) U.S.P./N.F. | 2.6 g |
| Blue Coloring F.D. & C. #1 | 1 drop (about 0.13 ml) |
| Sodium Carbonate, Anhydrous U.S.P./N.F. | to adjust pH to 7.0 |

In the example, Xylitol, derived from the cell walls of plants, as been proven to inhibit the growth of bacteria, in particular Strep Mutans, the main bacteria responsible for dental caries. Contrary to Fluoride, Xylitol can be safely ingested. Potassium Citrate is preferred as a sequestrant due to its solubizing and pH-stablilizing properties.

The preparation in the example was obtained according to the following steps:

Heating the water to approximately 66 degrees Celsius (150° F.);

Dissolving the oil of Spearmint, oil of Peppermint, Menthol and Glycerin in the Ethanol, and stirring the mixture into the heated water. The Polysorbate 20, Poloxamer 338 and Potassium Citrate were then sequentially dissolved into the heated water. Next, the Disodium Edetate solution was added within a range of 200 mg to 800 mg, i.e., from 2 to 8 mg of pure Disodium. After letting the preparation cool to approximately 49 degrees Celsius (120° F.), the Xylitol was added. After letting the preparation cool to approximately 43 degrees Celsius (110° F.), the approximately 38 degrees Celsius (100° F.), the blue coloring agent is added.

The pH was then adjusted to 7.0 with Sodium Carbonate. It should be noted that the preparation was continuously stirred during the entire process. Finally, the preparation was filtered through a 616-20 paper.

Before bottling for commerical distribution, the preparation is passed through an ultra-violet disinfection unit then further filtered through a 5 micron filter prior to bottling.

While the preferred embodiments of the invention has been described, modifications can be made and other embodiments may be devised without departing from the spirit of the invention and the scope of the appended claims.

What is claimed is:

1. A dental hygiene preparation which comprises an aqueous solution:

a sequestrant taken from a group consisting essentially of Sodium Citrate, Sodium Tripolyphosphate, Sorbitol and Potassium Citrate in a concentration of approximately 0.00132 to 0.032 percent per weight;

a saturated solution of Disodium Edetate in a concentration of approximately 0.0003 to 0.04 percent per volume;

an emulsifying agent; and

Xylitol in a concentration of 0.008 to 0.08 percent per weight.

2. The preparation of claim 1 which further comprises a sweetener taken from a group consisting essentially of Aspartame and Sodium Saccharine Dihydrate.

3. The preparation of claim 1, wherein said emulsifying agent is taken from a group consisting essentially of Poloxamer and Polysorbate.

4. The preparation of claim 3, wherein said sweetener is in a concentration of 0.026 to 0.66 percent per weight.

5. The preparation of claim 4, wherein said sweetener consists of Aspartame.

6. The preparation of claim 4, in the absence of any effective amount of free Fluoride-providing compound.

7. The preparation of claim 4, which further comprises at least one flavoring agent taken from a group consisting essentially of Spearmint and Menthol.

8. The preparation of claim 4, which further comprises a ph-adjusting compound in proportion necessary to set a ph of approximately 7.0.

9. The preparation of claim 4, which further comprises approximately 0.02 percent per weight.

10. The preparation of claim 8, wherein said ph-adjusting agent comprises Sodium Carbonate Anhydrous.

11. A dental hygiene preparation which comprises:

a sequestrant taken from a group consisting essentially of Potassium Citrate, Sodium Citrate, Sodium Tripolyphosphate Sorbitol;

Disodium Edetate; and

Xylitol.

12. The preparation of claim 11 in the absense of any effective amount of free fluoride-providing compound.

13. The preparation of claim 11 which further comprises:

an emulsifying agent; and a flavoring agent.

14. The preparation of claim 13, wherein said emulsifying agent is taken from a group consisting essentially of Poloxamer and Polysorbate.

15. The preparation of claim 11 which comprises:

water;

Potassium Citrate from 13 milligram to 317 milligrams per liter of water;

Disodium Edetate from 0.5 milligrams to 2.0 milligrams per liter of water;

Xylitol from 0.25 grams to 2.65 gram per liter of water; and an emulsifying agent from 13 to 317 milligrams per liter of water.

16. The preparation of claim 15 in the absense of any effective amount of free-Fluoride-providing agent.

17. The preparation of claim 15, wherein said emulsifying agent is taken from a group consisting essentially of Poloxamer and Polysorbate.

18. The preparation of claim 15, wherein said emulsifying agent comprises Polysorbate from approximately 0.13 milliliters to 3.17 milliliters per liter of water.

19. The preparation of claim 15, wherein said emulsifying agent comprises Poloxamer from approximately 13.2 milligrams to 317 milligrams per liter of water.

20. The preparation of claim 17 which further comprises at least one sweetener from 2 grams to 25 grams per liter of water.

21. The preparation of claim 17 which further comprises Calcium Ascorbate Dihydrate from 26 milligrams to 317 milligrams per liter of water.

* * * * *